(12) United States Patent
Feiertag

(10) Patent No.: US 11,298,016 B2
(45) Date of Patent: Apr. 12, 2022

(54) POSITIONING UNIT AND EXAMINATION DEVICE

(71) Applicant: Oculus Optikgeraete GmbH, Wetzlar (DE)

(72) Inventor: Carsten Feiertag, Hungen (DE)

(73) Assignee: OCULUS OPTIKGERAETE GMBH, Wetzlar (DE)

( * ) Notice: Subject to any disclaimer, the term of this patent is extended or adjusted under 35 U.S.C. 154(b) by 335 days.

(21) Appl. No.: 16/672,732

(22) Filed: Nov. 4, 2019

(65) Prior Publication Data

US 2020/0138287 A1 May 7, 2020

(30) Foreign Application Priority Data

Nov. 5, 2018 (DE) ...................... 10 2018 127 469.6

(51) Int. Cl.
*A61B 3/13* (2006.01)
(52) U.S. Cl.
CPC ...................... *A61B 3/13* (2013.01)
(58) Field of Classification Search
CPC .................................. A61B 3/13; A61B 3/14
USPC ...................................................... 351/205
See application file for complete search history.

(56) References Cited

U.S. PATENT DOCUMENTS

| 4,833,382 | A | * | 5/1989 | Gibbs | G02B 21/26 |
| | | | | | 318/640 |
| 6,474,815 | B1 | * | 11/2002 | Ulbers | A61B 3/135 |
| | | | | | 351/214 |
| 2013/0229706 | A9 | | 9/2013 | Feiertag et al. | |
| 2017/0042419 | A1 | * | 2/2017 | Nakanishi | A61B 90/30 |

FOREIGN PATENT DOCUMENTS

| DE | 102011002940 A1 | 7/2012 |
| JP | 2008093433 A | 4/2008 |
| JP | 2012148078 A | 8/2012 |

OTHER PUBLICATIONS

Japan Patent Office, Office Action, Application No. 2019-199868, dated Jan. 5, 2022, 3 pages [English Language Translation Only].

* cited by examiner

*Primary Examiner* — Mohammed A Hasan
(74) *Attorney, Agent, or Firm* — Quarles & Brady LLP

(57) ABSTRACT

A positioning unit for positioning an optical unit in an optical path of a microscope between a microscope lens and in front of an eye to be examined includes a connection device coupling the positioning unit to the microscope. The positioning unit includes an accommodating device configured to adapt an ophthalmoscopic lens that serves to examine an ocular fundus to the positioning unit as an optical element of the optical unit. The positioning unit includes a positioning device to move the ophthalmoscopic lens relative to the microscope in the longitudinal direction of the optical path. The accommodating device presents an adjusting means for displacing the ophthalmoscopic lens in an adjusting plane that runs orthogonally relative to the optical path of the microscope.

16 Claims, 2 Drawing Sheets

POSITIONING UNIT AND EXAMINATION DEVICE

This application claims priority to German Patent Application No. 10 2018 127 469.6 filed Nov. 5, 2018. The contents of this application are hereby incorporated by reference as if set forth in their entirety herein.

The disclosure relates to a positioning unit for positioning an optical unit in an optical path of a microscope between a microscope lens and in front of an eye to be examined, said positioning unit comprising a connection device with the aid of which the positioning unit is coupled to the microscope, said positioning unit comprising an accommodating device by means of which an ophthalmoscopic lens that serves to examine an ocular fundus is adaptable to the positioning unit as an optical element of the optical unit, said positioning unit comprising a positioning device by means of which the ophthalmoscopic lens is moved relative to the microscope in the longitudinal direction of the optical path. Furthermore, the disclosure relates to an examination device having a positioning unit.

Microscopes for carrying out eye surgeries are routinely used for surgeries in a front section of an eye. If such surgical interventions are also performed in a rear section of the eye, it is necessary to add an examination device, which makes it possible to bring this particular area of the eye into focus, to the microscope. Such examination devices comprise at least one wide-angle lens or ophthalmoscopic lens for examining the wide angle of the relevant rear part of the eye, said ophthalmoscopic lens providing an intermediate image in an optical path in front of a microscope, which intermediate image can be brought into focus with the aid of the microscope. For bringing the intermediate image into focus, the length of the optical path of the microscope has to be shortened, which can be done by way of the corresponding setting means at the microscope. Since, however, switching between different views, with and without an ophthalmoscopic lens, is required during an eye surgery, such a setting of the microscope is an obstacle, which is why a reducing lens may be provided in the optical path in front of the microscope lens, said reducing lens serving to shorten the optical path of the microscope and being used together with the ophthalmoscopic lens. The two lenses are retained by a positioning unit of the examination device, which positioning unit is directly fastened to the microscope, and can be positioned in the optical path as required, without the microscope having to be substantially adapted during a surgery. The positioning unit routinely comprises a connection device by means of which the positioning unit can be coupled to the microscope. Furthermore, the positioning unit is realized in such a way that the relevant lenses can simply be pivoted or slid into the optical path and removed from the same again.

In order to be able to adapt the intermediate image of the ophthalmoscopic lens to a focal length of the microscope lens as precisely as possible, the ophthalmoscopic lens is routinely realized so as to be settable along the optical path of the microscope. Such a longitudinal shift of the ophthalmoscopic lens can mechanically be realized in different manners. Apart from a longitudinal shift of the ophthalmoscopic lens with the aid of a threaded drive made of metal, it is, inter alia, known from DE 10 2011 002 940 to realize the positioning unit mainly from a plastic material and to realize the longitudinal shift of the ophthalmoscopic lens via a double rocker mechanism. The advantage of this positioning unit is that the positioning unit can be produced at low costs, for instance in an injection molding method, which makes it possible, in terms of profitability, to use the positioning unit and/or the examination device as throwaway products. It is then not at all necessary anymore to sterilize the positioning unit and the examination device, which is normal otherwise. The disadvantage here is, however, that plastics, in contrast to metal, in particular in the case of fragile rocker bar mechanisms, cannot always be produced with the desired precision that is required for the ophthalmoscopic lens to be positioned. In this way, due to the selected plastics injection molding method, to an injection molding tool, to a storage of the finished positioning units or also due to other factors, the positioning unit may go out of shape caused by tension, which may lead to unacceptable deviations in the dimensions of the positioning unit.

The present disclosure is therefore based on the object of proposing a positioning unit and an examination device that make more precise positioning possible.

This object is attained by a positioning unit having the features of claim 1, by an examination device having the features of claim 14 and by a microscope having the features of claim 16.

The positioning unit in accordance with the disclosure for positioning an optical unit in an optical path of a microscope between a microscope lens and in front of an eye to be examined comprises a connection device by means of which the positioning unit is coupled to the microscope, said positioning unit comprising an accommodating device with the aid of which an ophthalmoscopic lens that serves to examine an ocular fundus is adaptable to the positioning unit as an optical element of the optical unit, said positioning unit comprising a positioning device by means of which the ophthalmoscopic lens is moved relative to the microscope in the longitudinal direction of the optical path, wherein the accommodating device presents an adjusting means by means of which the ophthalmoscopic lens is displaceable in an adjusting plane that runs orthogonally relative to the optical path of the microscope.

The positioning unit is configured to be fastened to the microscope or to the microscope lens in an easy way by means of the connection device and the ophthalmoscopic lens can be retained in the optical path of the microscope lens, between the eye to be examined and the microscope lens. Here, it is envisaged to dispose the ophthalmoscopic lens in such a way that a main axis or optical axis of the microscope lens runs through a center of the ophthalmoscopic lens. The ophthalmoscopic lens can be disposed in this way particularly easily with the positioning unit in that the accommodating device presents the adjusting means by means of which the ophthalmoscopic lens can be displaced relative to the optical path or to the microscope lens axis. The ophthalmoscopic lens can then be shifted in the adjusting plane, which runs orthogonally in relation to the microscope lens axis, until a center or a main axis of the ophthalmoscopic lens and the optical axis of the microscope lens are aligned. Then, it is also irrelevant in principle if the positioning unit is particularly dimensionally stable since a readjustment of the ophthalmoscopic lens is always possible by means of the adjusting means. Positioning units that otherwise are considered to be potentially defective and that would have to be declared to be waste can then be used, whereby the positioning unit can on the whole be produced at lower costs. Moreover, by way of the possibility to correct the position of the ophthalmoscopic lens in the optical path of the microscope, an improved use of the positioning unit becomes possible since a particularly precise image of the eye can be examined with the aid of the positioning unit.

The accommodating device can realize a retaining means for retention of the ophthalmoscopic lens and the connection thereof with the positioning device. The accommodating device in this way makes it possible to realize the ophthalmoscopic lens separately from the positioning unit and to exchange the ophthalmoscopic lens as required, for instance during an eye surgery, without having to replace the entire positioning unit. It is then also left to the surgeon to add the positioning unit having the ophthalmoscopic lens to the examination device as required. In order to make a standardized connection of the ophthalmoscopic lens with the accommodating device possible, the ophthalmoscopic lens can be retained in the predetermined position by the retaining means, said retaining means, in connection with the accommodating device of the positioning unit, being realized in the manner of a plug-in connection, for example. By way of this interface at the positioning unit, different types of ophthalmoscopic lenses can be adapted to the positioning unit. In order to ensure that the ophthalmoscopic lens is used only once, it may also be envisaged to realize to retaining means in such a way that it is destroyed when the retaining means and the ophthalmoscopic lens are detached. A connecting element can hence be envisaged at the retaining means, said connecting element being realized, for instance, in the manner of a detent element having a predetermined breaking point and being snapped into place when assembling the component in such a way that demounting is only possible in a way in which the connecting element is inevitably destroyed. The retaining means can be realized in the manner of a plug accommodation into which a pin-shaped retaining bracket of the ophthalmoscopic lens can be plugged.

The retaining means can be disposed at the positioning device so as to be pivotable about an axis that is realized so as to be parallel to the optical path of the microscope. This way of disposing the retaining means makes it possible to pivot the ophthalmoscopic lens at the positioning unit orthogonally in the optical path of the microscope or to position it within the adjusting plane. The adjusting plane is then the plane within which the ophthalmoscopic lens can be pivoted. This also ensures that a distance of the ophthalmoscopic lens relative to the microscope lens stays the same, i.e. remains unchanged while the ophthalmoscopic lens is pivoted. The axis can be realized at the positioning unit itself or at the retaining means in the manner of a pin-shaped extension, which can be plugged into a bearing recess in the retaining means or positioning device. The pin-shaped extension can in this case also be locked together with the bearing recess so that no particular fastening of the retaining means at the positioning device is required.

The adjusting means can be realized from a coupling gearing that is realized between the positioning device and the retaining means. The coupling gearing can present at least one coupling member that makes it possible to displace the positioning device relative to the retaining means in the direction of the adjusting plane in such a manner that the ophthalmoscopic lens is pivotable at the axis of the retaining means or of the positioning device. By means of the coupling member or coupling gearing, the ophthalmoscopic lens can then be pivoted or adjusted.

The coupling gearing can be realized so as to have a transmission between a path of displacement of the ophthalmoscopic lens and an actuating path of the adjusting means, wherein said path of displacement can be smaller than the actuating path. In this way, it is advantageously possible to procure a small path of displacement with a comparatively large actuating path and consequently set the ophthalmoscopic lens in a particularly precise way. Since this adjustment of the ophthalmoscopic lens is conducted manually by way of a surgeon, a particularly precise correction of the position of the ophthalmoscopic lens can always be ensured as required.

The adjusting means can present an adjusting lever that can be linked to the positioning device via a first adjusting axis and to the retaining means via a second adjusting axis, which is spaced apart from the first adjusting axis in the direction of the adjusting plane. The adjusting lever can in this case correspond to a coupling member, which is in each instance linked to the positioning device and to the retaining means via the adjusting axes. Since the first adjusting axis and the second adjusting axis are spaced apart from each other, it becomes possible, by way of a movement of the adjusting lever, to bring about a movement of the positioning device relative to the retaining means in the direction of the adjusting plane, i.e. orthogonally with respect to the optical path of the microscope, said retaining means or the positioning device being configured to be pivoted relative to each other about the axis that is realized between the retaining means and the positioning device. The first and the second adjusting axis can in each instance be realized as a pin-type extension and be in each instance inserted in turn into a recess or bearing accommodation that is realized in an analog way. The respective pin-shaped extension can then also be locked together with the bearing accommodation. The adjusting axes can be realized at the adjusting lever or at the positioning device or at the retaining means, wherein the respective bearing accommodation can be realized at the positioning device or at the retaining means or at the adjusting lever.

The adjusting lever can be realized by a plate at the longitudinal ends of which gripping edges, which serve to be seized between fingertips, are realized. The plate can thus be realized in such a way that it is disposed between the retaining means and the positioning device. A simple operation of the adjusting means becomes possible in that the plate is seized with fingertips at its longitudinal ends and is moved by rotating it about the first adjusting axis. The plate then brings about a movement of the second adjusting axis and, as a result, of the retaining means with the ophthalmoscopic lens in the adjusting plane. The plate can be realized so as to be in one piece and can present the first adjusting axis and the second adjusting axis.

As an alternative, the adjusting lever can be realized so as to have an actuating end, which serves to be seized between fingertips. The actuating end can be molded to the adjusting lever or be realized in the manner of an elongation of the adjusting lever.

The adjusting means can present an adjusting axis having an eccentric, wherein said adjusting axis can be linked to the positioning device and to the retaining means, wherein said eccentric can extend at the positioning device or at the retaining means in the direction of the adjusting plane. The eccentric can then in principle realize an adjusting lever in that the eccentric rests against the positioning device or against the retaining means, making a relative shift of the positioning device and of the retaining means possible. Here, the adjusting axis can be realized as a pin-shaped extension to which the eccentric is molded. The adjusting axis can be inserted into a bearing recess in the positioning device or in the retaining means, depending on whether the eccentric rests against the positioning device or against the retaining means.

The positioning unit can realize a fitting for accommodating a reducing lens as another optical element of the optical unit. The fitting can be disposed so as to be directly adjacent to the microscope lens if the positioning unit is fastened to the microscope.

A movability of the ophthalmoscopic lens in the longitudinal direction of the optical path makes it possible to adapt the optical unit to the eye to be examined and/or to adapt the optical path of the microscope to an intermediate image that is situated in the optical path without having to change the settings of the microscope to this effect.

The positioning device can comprise a setting means by means of which a position of the ophthalmoscopic lens can be set in the longitudinal direction of the optical path. In this way, it is possible, for bringing the intermediate image into focus, to change the corresponding setting of the ophthalmoscopic lens or to correct the position of the ophthalmoscopic lens in the optical path in the longitudinal direction of the optical path. In this way, it can be ensured that the ophthalmoscopic lens is situated in the respective desired position, the setting or positioning of the ophthalmoscopic lens for instance being effected manually through a surgeon. The setting means, in a particularly simple embodiment, can be formed from a setting wheel having a worm gearing or an eccentric gearing. For instance, the setting means can be manufactured as an injection molded article that can simply be plugged onto a hub and engaging with a coupling gearing of the positioning device for longitudinal adjustment of the ophthalmoscopic lens.

The connection device can be realized so as to have a hinge that comprises at least one detent means by means of which the optical unit is lockable in a position of use in the optical path and/or in a position of nonuse outside of the optical path. The hinge can be realized between the connection device and the positioning device so that it is possible to pivot the positioning device relative to the connection device. Furthermore, the detent means can be realized at the connection device and at the positioning device, which, for her part, can be realized from a detent lug and from detent indentations for engaging with the detent lug. The detent lug and the detent indentations can each be molded to the connection device or to the positioning device. The detent indentations can then be disposed in such a way that the detent lug, in the position of use or in the position of nonuse, in each instance engages with a detent indentation, in this way making it possible to lock the optical unit or the positioning device.

The positioning unit can be realized from plastic material, at least mainly, preferably completely. In this way, the costs of production for the positioning unit can be reduced considerably since the components of the positioning unit can be produced at low costs, for instance in an injection molding process. The cost savings that can be achieved by using plastic material makes it possible to entirely do without reusing the positioning unit and to dispose of the positioning unit after having used it. Thereby, more cost benefits arise since no costs for sterilization and maintenance are incurred. By using the positioning unit only once, risks of contamination and possible defects at the positioning unit that are connected with sterilization can furthermore also be eliminated.

The examination device in accordance with the disclosure comprises a positioning unit in accordance with the disclosure and an optical unit, an optical element of the optical unit being an ophthalmoscopic lens. Furthermore, it may be envisaged that the ophthalmoscopic lens is realized so as to be in one piece. The ophthalmoscopic lens can in this case also be produced from a plastic material having the corresponding optical quality.

Another optical element of the optical unit can be realized as a reducing lens that serves to adapt the optical path.

The microscope in accordance with the disclosure presents an examination device in accordance with the disclosure.

Other advantageous embodiments of the examination device or of the microscope result from the description of the features contained in the dependent claims that relate back to claim 1.

In the following, a preferred embodiment of the disclosure is explained in more detail with reference to the enclosed drawing.

Figure 1:
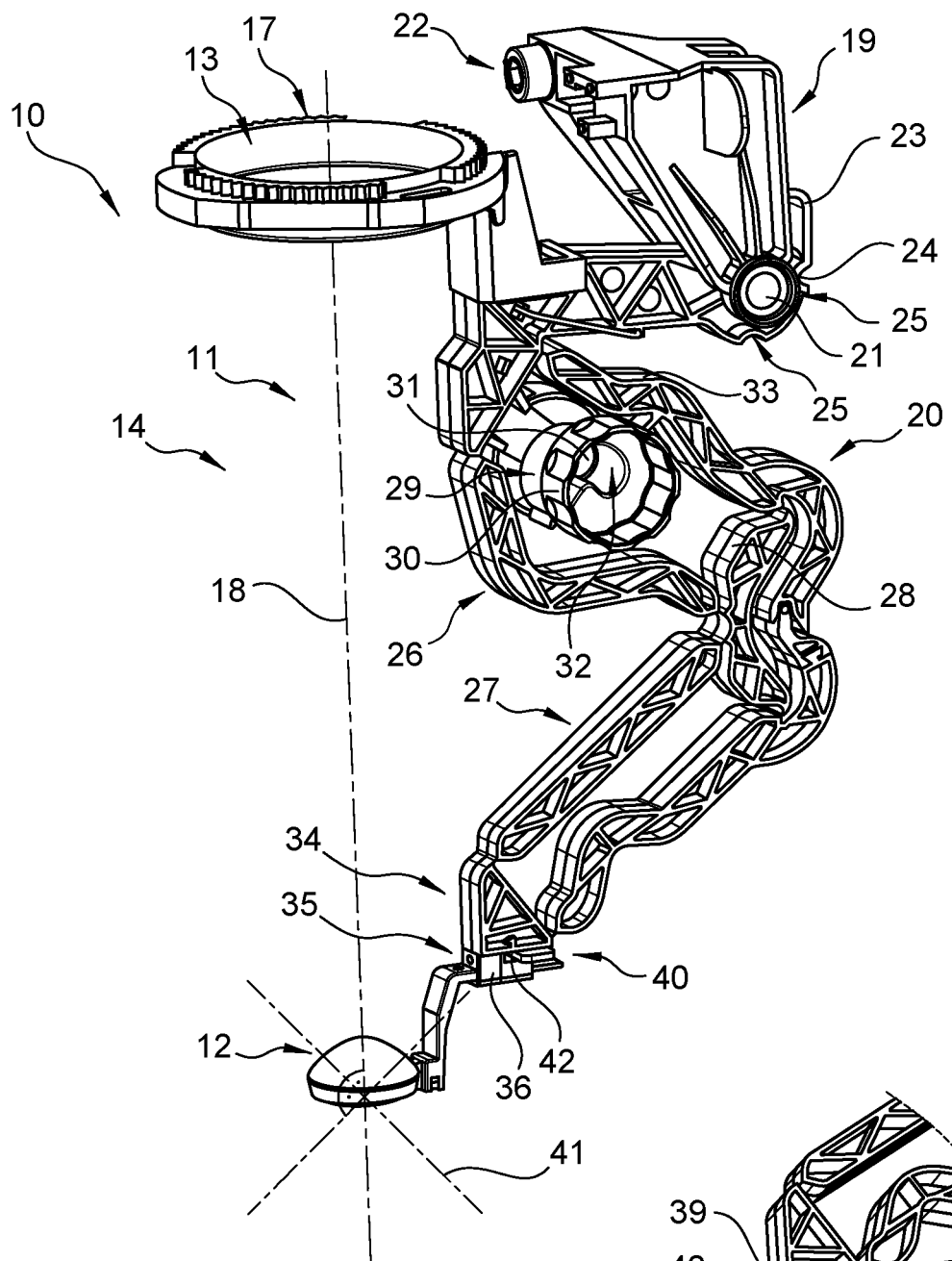
FIG. 1 shows a perspective illustration of an examination device having a positioning unit in an operating position.
Figure 2:
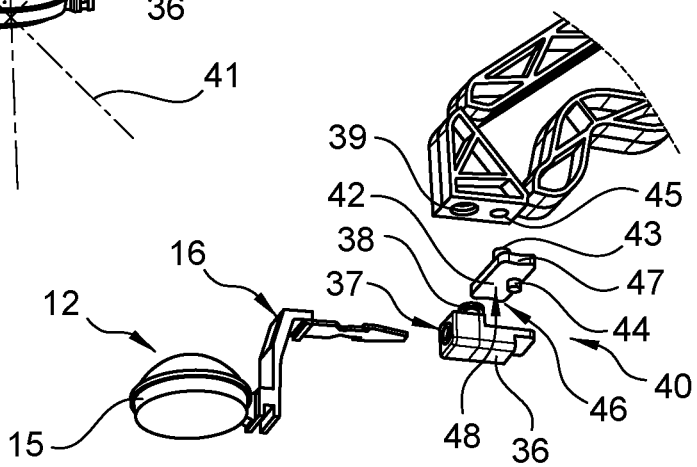
FIG. 2 shows a perspective exploded illustration of an adjusting means of the positioning unit from FIG. 1.

A combined view of FIGS. 1 and 2 shows an examination device 10 having a positioning unit 11 and an ophthalmoscopic lens 12 as well as a reducing lens 13. The ophthalmoscopic lens 12 and the reducing lens 13 form an optical unit 14 that can be adapted to the positioning unit 11. The ophthalmoscopic lens 12 is realized so as to have a fitting 15 and a pin-shaped retaining bracket 16. The reducing lens 13 is inserted into a fitting 17 of the positioning unit 11. By means of the positioning unit 11, the ophthalmoscopic lens 12 and the reducing lens 13 can be positioned underneath a microscope lens that is not illustrated here, in such a way that an optical axis of the microscope lens is aligned with an optical axis 18 of the optical unit 14. An optical path of the microscope then runs through the optical unit 14 or along the optical axis 18.

The positioning unit 11 comprises a connection device 19 and a positioning device 20, a hinge 21 for pivoting the positioning device 20 with the optical unit 14 out of and into the optical path of the microscope being realized between the connection device 19 and the positioning device 20. The connection device 19 presents engagement elements 22 for linking the connection device 19 to an adapter means of a microscope that is not illustrated here. Furthermore, the connection device 19 realizes a plate spring 23 having a cam 24 that can engage with detent recesses 25 at the positioning device 20. In this way, it is possible to pivot the positioning device 20 and the hinge 21 and to lock them in the position of use that is illustrated here or in a position of nonuse outside of the optical path.

The positioning device 20 is realized from a first double rocker mechanism 26 and from a second double rocker mechanism 27 that are linked to each other via a coupling member 28. The double rocker mechanisms 26 and 27 present a gear transmission ratio 1:1 and in this way make it possible to move the ophthalmoscopic lens 12 along the optical axis 18. This movement of the ophthalmoscopic lens 12 can be effected by means of a setting means 29 that is realized here from a setting wheel 30, from an axis 31 and from a screw curve 32 that is molded thereto. Turning the setting wheel 30 makes the screw curve 32 roll off at a rocker 33 of the first double rocker mechanism 26 and, as a result, brings about the ophthalmoscopic lens 12 being lifted or lowered.

An accommodating device 35 for accommodating and adapting the ophthalmoscopic lens 12 or its retaining bracket 16 is disposed at a lower end 34 of the positioning device 20. The accommodating device 35 presents a retaining means 36 that realizes an accommodation 37 for the retaining bracket 16 into which the retaining bracket 16 is plugged, being able to be snapped into place there. Furthermore, an axis 38 that is plugged into a bearing recess 39 in the positioning device 20 and snapped into place there is realized at the retaining means 36. The accommodating device 35 furthermore presents an adjusting means 40 by means of which the ophthalmoscopic lens 12 can be displaced in an adjusting plane 41 that runs orthogonally relative to the optical path of the microscope. The adjusting means 40 is realized by means of a plate 42 and of the retaining means 36, said plate 42 realizing a first adjusting axis 43 and a second adjusting axis 44. The first adjusting axis 43 is inserted into another bearing recess 45 that is realized in the positioning device 20, said second adjusting axis 44 being inserted into a bearing recess in the retaining means 36 that is not visible here. The first adjusting axis 43, relative to the second adjusting axis 44, is spaced apart from the same so that a rotational movement of the plate 42 about the first adjusting axis 43 brings about a pivoting of the retaining means 36 about the axis 38. For pivoting the plate 42, the same, at its respective longitudinal ends 46, presents gripping edges 47, which can easily be seized between fingertips and make it possible to easily turn the plate 42 about the first adjusting axis 43 with fine motor skills. The plate 42 realizes an adjusting lever 48 with the first adjusting axis 43 and the second adjusting axis 44, with the aid of which an actuating path of the plate 42 can be transformed into a path of displacement of the ophthalmoscopic lens 12. Here, the path of displacement is smaller than the actuating path so that a precise adjustment of the ophthalmoscopic lens 12 becomes possible.

Figure 3A:
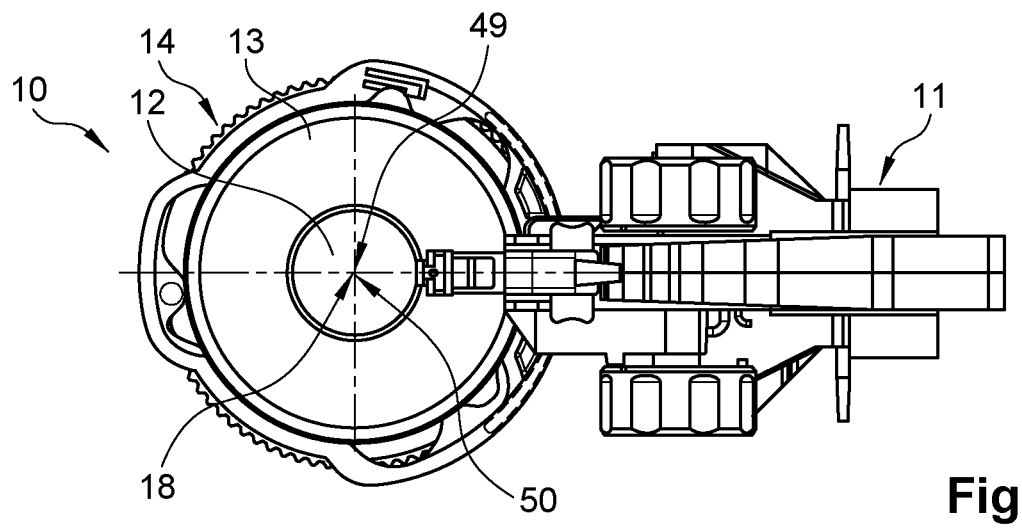
FIGS. 3a to 3c show the examination device from FIG. 1 in a view from above with different positions of an ophthalmoscopic lens.
Figure 3B:
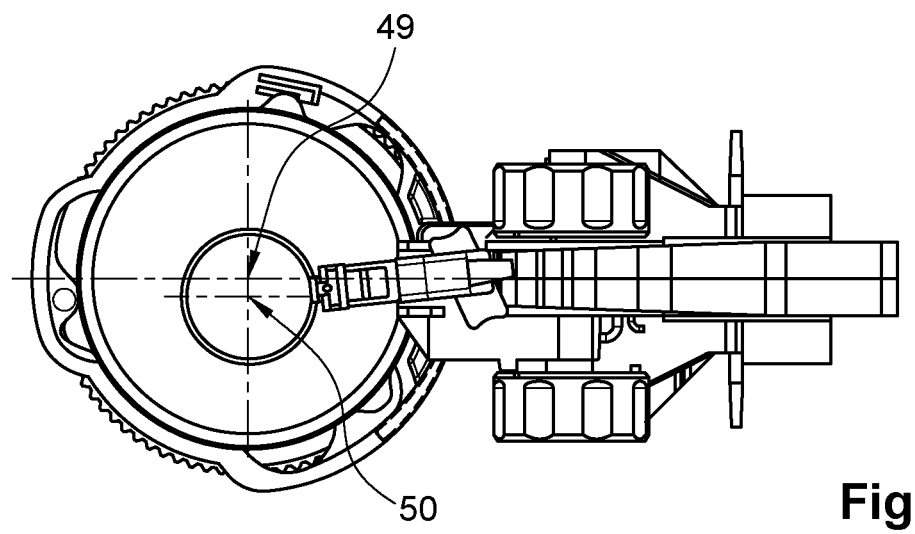
Figure 3C:
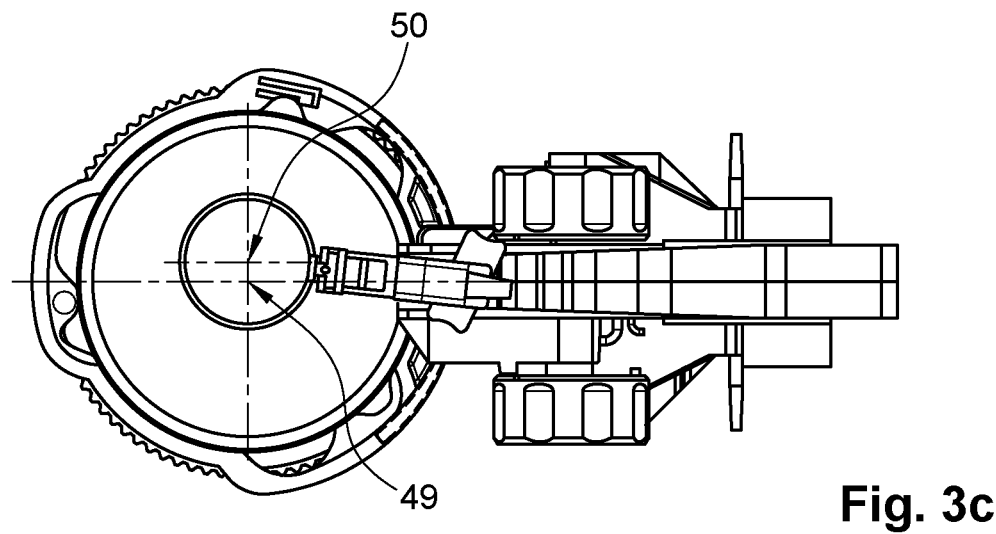

FIGS. 3a to 3c show a possible displacement of the ophthalmoscopic lens 12 relative to a center 49 of the reducing lens 13. In accordance with FIG. 3a, the ophthalmoscopic lens 12 is disposed so as to be concentrical relative to the reducing lens 13 and the center 49 of the reducing lens 13 is aligned with a center 40 of the ophthalmoscopic lens 12 in such a manner that the optical axis 18 runs through the centers 49 and 50. It is not required here to specifically adjust or set the reducing lens 13 since the same can be disposed so as to be directly underneath the microscope lens. Therefore, it is only required to adjust the ophthalmoscopic lens 12 on grounds of potential dimensional variations of the positioning device 20, taking the reducing lens 13 as a reference. FIGS. 3b and 3c each show an offset of the ophthalmoscopic lens 12 or of the reducing lens 13 relative to the optical axis 18 so that the centers 49 and 50 are not aligned any more. Here, this offset results from the plate 42 and, as a result, the retaining means 36 being pivoted about the axis 38.

The invention claimed is:

1. A positioning unit for positioning an optical unit in an optical path of a microscope between a microscope lens and in front of an eye to be examined, said positioning unit comprising a connection device coupling the positioning unit to the microscope, said positioning unit comprising an accommodating device configured to adapt an ophthalmoscopic lens that serves to examine an ocular fundus to the positioning unit as an optical element of the optical unit, said positioning unit comprising a positioning device moving the ophthalmoscopic lens relative to the microscope in the longitudinal direction of the optical path,
wherein
the accommodating device presents an adjusting device configured to displace the ophthalmoscopic lens in an adjusting plane that runs orthogonally relative to the optical path of the microscope.

2. The positioning unit according to claim 1,
wherein
the accommodating device realizes a retaining device for retention of the ophthalmoscopic lens and the connection thereof with the positioning device.

3. The positioning unit according to claim 2,
wherein
the retaining device is disposed at the positioning device so as to be pivotable about an axis that is realized so as to be parallel to the optical path of the microscope.

4. The positioning unit according to claim 2,
wherein
the adjusting device is realized from a coupling gearing that is realized between the positioning device and the retaining device.

5. The positioning unit according to claim 4,
wherein
the coupling gearing is realized so as to have a transmission between a path of displacement of the ophthalmoscopic lens and an actuating path of the adjusting device, said path of displacement being smaller than the actuating path.

6. The positioning unit according to claim 2,
wherein
the adjusting device presents an adjusting lever that is linked to the positioning device via a first adjusting axis and to the retaining device via a second adjusting axis, which is spaced apart from the first adjusting axis in the direction of the adjusting plane.

7. The positioning unit according to claim 6,
wherein
the adjusting lever is realized by a plate at the longitudinal ends of which gripping edges, which serve to be seized between fingertips, are realized.

8. The positioning unit according to claim 6,
wherein
the adjusting lever is realized so as to have an actuating end, which serves to be seized between fingertips.

9. The positioning unit according to claim 1,
wherein
the adjusting device presents an adjusting axis having an eccentric, said adjusting axis being linked to the positioning device and to the retaining device, said eccentric extending at the positioning device or at the retaining device in the direction of the adjusting plane.

10. The positioning unit according to claim 1,
wherein
the positioning unit realizes a fitting for accommodating a reducing lens as another optical element of the optical unit.

11. The positioning unit according to claim 1,
wherein
the positioning device comprises a setting device adapted to position the ophthalmoscopic lens can be set in the longitudinal direction of the optical path.

12. The positioning unit according to claim 1,
wherein
the connection device is realized so as to have a hinge that comprises at least one detent device adapted to lock the optical unit in a position of use in the optical path and/or in a position of nonuse outside of the optical path.

13. The positioning unit according to claim 1,
wherein
the positioning unit is composed of plastic material.

14. An examination device having a positioning unit according to claim 1 and having an optical unit, an optical element of the optical unit being an ophthalmoscopic lens.

15. The examination device according to claim 14, wherein
    another optical element of the optical unit is realized as a reducing lens that serves to adapt the optical path.

16. A microscope having an examination device according to claim 15.

* * * * *

UNITED STATES PATENT AND TRADEMARK OFFICE
CERTIFICATE OF CORRECTION

| | |
|---|---|
| PATENT NO. | : 11,298,016 B2 |
| APPLICATION NO. | : 16/672732 |
| DATED | : April 12, 2022 |
| INVENTOR(S) | : Carsten Feiertag |

It is certified that error appears in the above-identified patent and that said Letters Patent is hereby corrected as shown below:

In the Claims

Column 8, Line 56, "lens can be set in" should be --lens in--.

Signed and Sealed this
Thirty-first Day of May, 2022

Katherine Kelly Vidal
*Director of the United States Patent and Trademark Office*